(12) United States Patent
Johns et al.

(10) Patent No.: US 7,393,659 B2
(45) Date of Patent: Jul. 1, 2008

(54) ANALYTICAL METHOD FOR THE DETERMINATION OF INFANT FORMULA PROTEIN DIGESTIBILITY IN VITRO

(75) Inventors: Paul W. Johns, Columbus, OH (US); Lucia Cheng, Buffalo Grove, IL (US); Lobat Dowlati, Gahanna, OH (US)

(73) Assignee: Abbott Laboratories, Abbott Park, IL (US)

( * ) Notice: Subject to any disclaimer, the term of this patent is extended or adjusted under 35 U.S.C. 154(b) by 502 days.

(21) Appl. No.: 10/464,052

(22) Filed: Jun. 18, 2003

(65) Prior Publication Data

US 2004/0047954 A1 Mar. 11, 2004

Related U.S. Application Data

(60) Provisional application No. 60/406,898, filed on Aug. 29, 2002.

(51) Int. Cl.
*C12Q 1/37* (2006.01)
*C12P 21/06* (2006.01)
*C12N 9/48* (2006.01)
*C12N 9/50* (2006.01)

(52) U.S. Cl. .................. 435/23; 435/68.1; 435/212; 435/219

(58) Field of Classification Search ............ 435/23, 435/68.2, 212, 219, 68.1; 530/343, 360, 530/365, 407, 833; 426/23, 24, 583, 657
See application file for complete search history.

(56) References Cited

U.S. PATENT DOCUMENTS

| | | | | |
|---|---|---|---|---|
| 3,480,511 A | * | 11/1969 | Jones | .................. 435/101 |
| 3,697,659 A | * | 10/1972 | Marco | .................. 514/673 |
| 4,981,704 A | | 1/1991 | Thibault | |
| 5,780,439 A | | 7/1998 | Mendy | |
| 5,952,193 A | | 9/1999 | Shimamura | |
| 5,993,795 A | * | 11/1999 | Osawa et al. | .................. 424/74 |
| 6,395,508 B1 | | 5/2002 | Shimamura et al. | |
| 6,413,779 B1 | | 7/2002 | Birouez-Aragon | |
| 6,451,552 B1 | | 9/2002 | Van Beresteijn | |

FOREIGN PATENT DOCUMENTS

EP       0 421 309 A2    9/1990

OTHER PUBLICATIONS

Garcia et al. "Determination of tryptophan content in infant formulas and medical nutritionals" J. AOAC International (1992) 75(6): 1112-1119.*
MacGregor et al. "Amino acid profiles of total and soluble protein in feedstuffs commonly fed to ruminants" J. Diary Sci. (1978) 61:566-573.*
Matoba et al. "Damage of amino acid residues of proteins after reaction with oxidizing lipids: Estimation by proteolytic enzymes" J. Food Sci. (1984) 49: 1082-1084.*
Barton-Wright, E.C. The Microbiological Assay of the "Essential" Amino-acids in Compound Feedingstuffs. Analyst. 1972, vol. 97, pp. 138-141.
Caric, et al. Evaluation of Protein Quality in a Human Milk Substitute by a Pepsin-Pancreatin Test. Mljekarstvo. 1984. vol. 34, No. 10, pp. 291-296, abstract only.
Rudloff S. and Lonnerdal B. Journal of Pediatric Gastroenterology and Nutrition, 15 (1992) 25-33.
Lindberg, T, et al. Journal of Pediatric Gastroenterology and Nutrition, 27 (1998) 30-36.
Lindberg, T, et al. Journal of Pediatric Gastroenterology and Nutrition, 24 (1997) 537-543.
Satterlee LD, et al. JAOAC, 65/4 (1982) 798-809.
Lonnerdal B., Protein Mechanism During Infancy, Nestle Nutrition Workshop Series, 33 (1994) 53-65.
Hsu HW, Journal of Food Science, 42/5 (1977) 1269-1273.
Bodwell CE, et al. Am J. Clin Nutr, 33 (1980) 677-686.
Rutherford SM and Moughan PJ, J Diary Sci, 81 (1998) 909-917.
Kitabatake N and Kinekawa YI, J Agric Food Chem, 46 (1998) 4917-4923.
Carbonaro M, et al., J Agric Food Chem, 45/1 (1997) 95-100.
Gauthier SF, et al., J Food Sci, 51/4 (1986) 960-964.
Lottspeich, F. and Zorbas, H.: "Bioanalytik", 1998, Spektrum Akademischer Verlag, Heidelberg Berlin, XP 002396009; ISBN: 3-8274-0041-4, p. 295.
Swaisgood, H.E. and Catignani, G.L.: "Protein digestibility: In Vitro Methods of Assessment", Advances in Food and Nutrition Research, vol. 35, 1991, pp. 185-236, XP008068012, United States, ISSN: 1043-4526, p. 213-215.

* cited by examiner

*Primary Examiner*—Sandra E. Saucier
*Assistant Examiner*—Susan Hanley
(74) *Attorney, Agent, or Firm*—Sandra E. Weida; William J. Winter

(57) ABSTRACT

A method for in vitro determination of the digestibility of proteins in a nutritional product. The method utilized gastric and intestinal enzymes that are standardized for in vitro digestion process that mimics the in vivo digestive process. Further, specificity in digestion is determined by an amino acid profile.

11 Claims, No Drawings

ANALYTICAL METHOD FOR THE DETERMINATION OF INFANT FORMULA PROTEIN DIGESTIBILITY IN VITRO

This application claims benefit of provisional application 60/406,898, filed Aug. 29, 2002, now expired.

FIELD OF THE INVENTION

The invention relates to a method for quantifying the digestibility of infant formula protein. More particularly, the present invention relates to the determination of the digestibility of the proteins by amino acid profile analysis of total and soluble portions of an infant formula sample digested in vitro with USP digestive enzymes.

BACKGROUND OF THE INVENTION

Infant formulas are commercially available in a variety of forms including ready-to-feed, concentrated liquid and powdered forms. Infant formulas typically contain casein and/or whey proteins intended to ensure that the infant fed the formula receives adequate amounts of amino acids and, in particular, the essential amino acids for proper nutrition. Two factors in determining the nutritional quality of food proteins are digestibility and bioavailability. Typically, these formulas contain a higher level of protein than the level found in human breast milk. Infant formulas are manufactured with higher levels of proteins to account for the assumed lower digestibility of the proteins.

Studies of infant formulas have shown that the processes used during the manufacture of these formulas have nutritional consequences such as lowered solubility and/or digestibility of the proteins in the formula. For example, heat treatment over extended periods of time that is used to produce concentrated liquid and ready-to-feed infant formulas has been shown to decrease digestibility of proteins. As a result of exposure to heat, proteins denature or aggregate, possibly altering their digestibility. The treatment of milk at high temperatures has also been studied and has been shown to increase reactions of amino acids with sugars known as Maillard reactions. These reactions have been shown to decrease the bioavailability of amino acids by limiting the accessibility of proteolytic enzymes.

In vivo protein digestion is a two-step process. The first step is exposure of the protein to the pre-digestive enzyme pepsin. The second step involves hydrolysis with pancreatic enzymes. The evaluation of amino acid availability in vivo is difficult because protein digestion products are carried quickly into, and absorbed by, the small intestine. Additionally, endogenous proteins may be present and may be digested and absorbed at rates different from proteins ingested as food or in the form of a dietary supplement. Therefore, in vitro analyses of the digestibility of proteins have been developed.

The evaluation of infant formula digestibility has been performed by enzymatic hydrolysis colorimetric analysis (degree of hydrolysis using TNBS) and size exclusion chromatographic techniques such as high performance liquid chromatography (HPLC). The accuracy and precision of the information provided by these approaches is compromised by the presence of insoluble protein and/or by spectrophotometric and chromatographic interferences.

In vitro digestions of infant formula have been conducted using the pre-digestive enzyme, pepsin, and pancreatin. The digestibility of proteins was determined by measuring the increased level of non-protein nitrogen (NPN) following the in vitro digestion process as determined by Kjeldahl analysis. However, the enzymes used in these studies included no standardization of enzyme activity and therefore the activity of the enzymes used in the digestion may vary significantly from lot to lot. Further, nitrogen analysis by Kjeldahl procedures lack specificity in the quantification of digested and undigested protein. Specificity in the types of amino acids digested provides better guidance as to the required formulations of nutritional products, including infant formula, to further ensure digestion and absorption of essential amino acids by infants who are fed the formula.

Digestive studies have included assays to determine the activity levels of proteins such as pepsin, trypsin and chymotrypsin used in the digestion process. Pepsin activity has been measured in terms of units of trichloroacetic acid (TCA)-soluble products. Trypsin and chymotrypsin activities have been measured in terms of hydrolysis rate for a particular amino acid. While determining the activity level of the enzymes to be used could improve standardization of such assays, the added steps of determining enzyme activity are cumbersome and time consuming.

There is a need for a method of in vitro protein digestibility determination that utilizes enzymes having standardized activity. There is further a need for the results of such method to provide specificity in amino acid digestibility.

The invention provides a method for determining the digestibility of proteins while providing specificity in the quantification of digested and total (digested and undigested) protein.

SUMMARY OF THE INVENTION

One embodiment of the invention is a method for determining the digestibility of proteins, the method includes the steps of digesting a sample of a nutritional product and a reagent blank with at least one enzyme; terminating the digestion process; determining the total concentration of each of a plurality of amino acids for the sample and the blank; determining the total tryptophan concentration for the sample and the blank; determining the soluble concentration of each of the plurality of amino acids for the sample and the blank; determining the soluble concentration of tryptophan for the sample and the blank; and calculating the percentage of soluble amino acids in the digested sample of nutritional product.

In another embodiment, the method comprises the steps of separating each of the digested sample and the blank into a first portion and a second portion; determining the total concentration of each of the plurality of amino acids for the first portion of the sample and the first portion of the blank; determining the total tryptophan concentration for the first portion of the sample and the first portion of the blank; separating each of the second portion of the sample and the second portion of the blank into a liquid phase and a solid phase; determining a soluble concentration of each of the plurality of amino acids in the liquid phase; and determining a soluble concentration of tryptophan in the liquid phase.

In another embodiment the separating step is selected from the group consisting of acidification, precipitation, centrifugation, filtration, and a combination of centrifugation and filtration.

In another embodiment, the step of calculating the percentage of soluble amino acids includes the steps of adding the total concentrations of the plurality of amino acids and tryptophan concentrations for the sample and the blank; determining the difference in total concentration of the plurality of amino acids and tryptophan between the sample and the blank; adding the soluble concentration of the plurality of amino acids and tryptophan concentration in the sample and the blank; determining the difference in soluble concentration of the plurality of amino acids and tryptophan concentration between the sample and the blank; dividing the difference in soluble concentrations by the difference in total concentrations to determine a quotient; and multiplying the quotient by 100.

In one embodiment, the nutritional product is infant formula.

In one embodiment, the digesting step uses one or more enzymes intended to mimic the environment of a human gastrointestinal tract.

In a further embodiment, the enzymes are selected from the group consisting of pepsin, peptidases, pancreatin proteinase, papain, trypsin and chymotrypsin.

In yet a further embodiment, the step of digesting the sample includes the steps of obtaining the sample of nutritional product; adjusting the pH to about 4.5; adding pepsin; incubating the sample; increasing the pH to about 7.0; adding pancreatin proteinase; and incubating the sample.

In a further embodiment, the step of terminating the digestion is immersing the sample in a boiling water bath.

DETAILED DESCRIPTION OF THE INVENTION

The proteins for which digestibility may be determined according to the present invention may be in many forms, including but not limited to, nutritional products, dietary supplements, pharmaceuticals or other products. They may be used at any age, for example by infants, children or adults. There may be particular value in using them during periods of rapid growth, such as infancy, childhood and adolescence. The proteins for which digestibility may be determined according to the invention may be incorporated into a nutritious "vehicle or carrier" which includes but is not limited to the FDA statutory food categories: conventional foods, foods for special dietary uses, dietary supplements and medical foods. Suitable sources of protein for nutritional products include milk, soy, rice, meat (e.g., beef), animal and vegetable (e.g., pea, potato), egg (egg albumen), gelatin, and fish. Suitable intact proteins include, but are not limited to, soy-based, milk-based, casein protein, whey protein, rice protein, beef collagen, pea protein, potato protein and mixtures thereof. Suitable protein hydrolysates also include, but are not limited to, soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, a combination of animal and vegetable protein hydrolysates, and mixtures thereof. Hydrolyzed proteins (protein hydrolysates) are proteins that have been hydrolyzed or broken down into shorter peptide fragments and amino acids. Such hydrolyzed peptide fragments and free amino acids are more easily digested. In the broadest sense, a protein has been hydrolyzed when one or more amide bonds have been broken. Breaking of amide bonds may occur unintentionally or incidentally during manufacture, for example due to heating or shear. For purposes of this invention, the term hydrolyzed protein means a protein which has been processed or treated in a manner intended to break amide bonds. Intentional hydrolysis may be effected, for example, by treating an intact protein with enzymes or acids. The hydrolyzed proteins that are preferably utilized in formulas according to this invention are hydrolyzed to such an extent that the ratio of amino nitrogen (AN) to total nitrogen (TN) ranges from about 0.1 AN to 1.0 TN to about 0.4 AN to about 1.0 TN, preferably about 0.25 AN to 1.0 TN to about 0.4 AN to about 1.0 TN. (AN:TN ratios given are for the hydrolysate protein source alone, and do not represent the AN:TN ratios given in the final pediatric nutritional formula product, since free amino acids may be added as a supplement and would alter the reported value.) Protein may also be provided in the form of free amino acids. A formula according to the invention is preferably supplemented with various free amino acids in order to provide a more nutritionally complete and balanced formula.

Amino acids are the individual building blocks of protein biosynthesis. Non-essential amino acids are those that are synthesized in the body from ammonia and various carbon sources. Non-essential amino acids include: Alanine (ALA), Serine (SER), Aspartic Acid (ASP), Glutamic acid (GLU), Cysteine (CYS), Tyrosine (TYR), Asparagine (ASN), Proline (PRO), Glycine (GLY), and Glutamine (GLN). The abbreviation "GLX" refers to GLU plus GLN and the abbreviation "ASX" refers to ASP plus ASN.

Essential amino acids are also required for protein synthesis in vivo and must be obtained from dietary sources. They are Isoleucine (ILE), Leucine (LEU), Lysine (LYS), Methionine (MET), Phenylalanine (PHE), Threonine (THR), Tryptophan (TRP), Valine (VAL), Histidine (HIS) and Arginine (ARG) (essential in young growing animals, but not in adults). Of the essential amino acids, tryptophan has the lowest daily intake requirement.

Direct inferences as to the digestibility of proteins may be drawn from analyses that determine the type and concentration of amino acids in solution (the soluble or digestible portion) after in vitro digestion and level of concentration of amino acids in the solid phase (the non-digestible portion) after digestion. Examples of suitable free amino acids for adding to formula include, but are not limited to, L-tryptophan, L-tyrosine, L-cysteine, L-taurine, L-methionine, L-arginine, and L-carnitine.

Soy

One component of the nutritional formula of this invention is soy protein. As described above, a number of soy protein sources may be considered. The soy protein is isolated from the soybean. The soybean is an excellent source of high quality protein where about 38% to 40% of the soybean is protein. Briefly (as shown in Scheme I), the processing of soybeans involves the extraction of the oil from the dehulled, and cracked soybeans leaving the defatted soybean flakes.

Scheme I
Soybean Processing

| SOYBEANS | Soy Oil | Flour | |
|---|---|---|---|
| | | Protein Concentrate | |
| | Defatted Soybean Flakes | Protein Isolate | |
| | | Whey | |
| | | Protein Fiber | |

The defatted soybean flakes are typically milled into flours; alcohol-extracted or alkoline/$H_2O$ extracted to remove flavor compounds and sugars to make protein concentrates; and processed with water to remove sugars and flavor compounds, precipitated and dried to make protein isolates. Whey and protein fiber are by-products of the above processes.

Nutritional Products

Nutritional products contain macronutrients, ie. fats, proteins and carbohydrates, in varying relative amounts depending on the age and condition of the intended user, and often contain micronutrients such as vitamins, minerals and trace minerals. The term "food" includes solids and liquids. The term "nutritional product" includes but is not limited to these FDA statutory food categories: conventional foods, foods for special dietary uses, medical foods and infant formulas. "Foods for special dietary uses" are intended to supply a special dietary need that exists by reason of a physical, physiological, pathological condition by supplying nutrients to supplement the diet or as the sole item of the diet. A "medical food" is a food which is formulated to be consumed or administered enterally under the supervision of a physician and which is intended for the specific dietary management of a disease or condition for which distinctive nutritional requirements, based on recognized scientific principles, are established by medical evaluation.

In addition, a "dietary supplement" is a product intended to supplement the diet by ingestion in tablet, capsule or liquid form and is not represented for use as a conventional food or as a sole item of a meal or the diet.

Infant Formulas

Infant formula refers to nutritional formulations that meet the standards and criteria of the Infant Formula Act, (21 USC §350(a) et. seq.) and are intended to replace or supplement human breast milk. Although such formulas are available in at least three distinct forms (powder, liquid concentrate and liquid ready-to-feed ("RTF"), it is conventional to speak of the nutrient concentrations on an "as fed" basis and therefore the RTF is often described, it being understood that the other forms reconstitute or dilute according to manufacturer's directions to essentially the same composition and that one skilled in the art can calculate the relevant composition for concentrated or powder forms.

"Standard" or "Term" infant formula refers to infant formula intended for infants that are born full term as a first feeding. The protein, fat and carbohydrate components provide, respectively, from about 8 to 10, 46 to 50 and 41 to 44% of the calories; and the caloric density ranges narrowly from about 660 to about 700 kcal/L (or 19-21 Cal/fl.oz.), usually about 675 to 680 (20 Cal/fl.oz.). The distribution of calories among the fat, protein and carbohydrate components may vary somewhat among different manufacturers of term infant formula. SIMILAC™ (Ross Products Division, Abbott Laboratories), ENFAMIL™ (Mead Johnson Nutritionals), and GOOD START™ (Carnation) are examples of term infant formula.

"Nutrient-enriched" formula refers to infant formula that is fortified relative to "standard" or "term" formula. The primary defining characteristic that differentiates nutrient-enriched formulas is the caloric density; a secondary factor is the concentration of protein. For example, a formula with a caloric density above about 700 Kcal/L or a protein concentration above about 18 g/L would be considered "nutrient-enriched". Nutrient-enriched formulas typically also contain higher levels of calcium (e.g. above about 650 mg/L) and/or phosphorus (e.g. above about 450 mg/L). Examples include Similac NEOSURE™ and Similac Special Care™ formulas.

The liquid and powder nutritional products for which protein digestibility of the present invention can be determined are manufactured by generally conventional techniques known to those skilled in the art. Briefly, three slurries are prepared, blended together, heat treated, standardized, spray dried (if applicable), packaged and sterilized (if applicable).

Liquid Products

A carbohydrate/mineral slurry is prepared by first heating water to an elevated temperature with agitation. Minerals are then added. Minerals may include, but are not limited to, sodium citrate, sodium chloride, potassium citrate, potassium chloride, magnesium chloride, tricalcium phosphate, calcium carbonate, potassium iodide and trace mineral premix. A carbohydrate source, such as one or more of lactose, corn syrup solids, sucrose and/or maltodextrin is dissolved in the water, thereby forming a carbohydrate solution. A source of dietary fiber, such as soy polysaccharide, may also be added. The completed carbohydrate/mineral slurry is held under agitation at elevated temperature until it is blended with the other slurries, preferably for no longer than about twelve hours.

An oil slurry is prepared by combining and heating the basic oil blend. The basic oil blend typically contains some combination of soy, coconut, palm olein, high oleic safflower or sunflower oil and medium chain triglycerides. Emulsifiers, such as diacetyl tartaric acid esters of mono, diglycerides, soy mono, diglycerides, and soy lecithin may be used. Any or all of the oil-soluble vitamins A, D, E (natural R,R,R form or synthetic) and K may be added individually or as part of a premix. Beta carotene, which can function as an in vivo antioxidant, may also be added, as may a stabilizer such as carrageenan. Oils containing specific LCPs important to this invention (e.g. DHA and AA) can be added to the oil slurry. Care must be used with these LCPs since they easily degrade and become rancid. The completed oil slurry is held under agitation until it is blended with the other slurries, preferably for a period of no longer than about twelve hours.

A protein in water slurry is prepared by first heating water to an appropriate elevated temperature with agitation. The protein source is then added to the water with agitation. Typically this protein source is intact or hydrolyzed milk proteins (e.g. whey, casein), intact or hydrolyzed vegetable proteins (e.g. soy), free amino acids and mixtures thereof. In general, any known source of amino nitrogen can be used in this invention. The completed protein slurry is held under agitation at elevated temperature until it is blended with the other slurries, preferably for a period no longer than about two hours. As an alternative, some protein may be mixed in a protein-in-fat emulsion rather than protein-in-water.

The protein in water and carbohydrate/mineral slurries are blended together with agitation and the resultant blended slurry is maintained at an elevated temperature. After a brief delay (e.g. a few minutes), the oil slurry is added to the blended slurry from the preceding step with agitation. As an alternative to addition to the oil blend, the LCP oils can be added directly to the blend resulting from combining the protein, carbohydrate/mineral and oil slurries.

After sufficient agitation to thoroughly combine all constituents, the pH of the completed blend is adjusted to the desired range. The blended slurry is then subjected to deaeration, ultra-high temperature heat treatment, emulsification and homogenization, then is cooled to refrigerated temperature. Preferably, after the above steps have been completed, appropriate analytical testing for quality control is conducted. Based on the analytical results of the quality control tests, and appropriate amount of water is added to the batch with agitation for dilution.

A vitamin solution, containing water soluble vitamins and trace minerals (including sodium selenate), is prepared and added to the processed slurry blend with agitation. A separate solution containing nucleotides is prepared and also added to the processed blended slurry with agitation.

The pH of the final product may be adjusted again to achieve optimal product stability. The completed product is then filled into the appropriate metal, glass or plastic containers and subjected to terminal sterilization using conventional technology. Alternatively, the liquid product can be sterilized aseptically and filled into plastic containers.

Powder Products

A carbohydrate/mineral slurry is prepared as was described above for liquid product manufacture.

An oil slurry is prepared as was described above for liquid product manufacture with the following exceptions: 1) Emulsifiers (mono, diglycerides, lecithin) and stabilizers (carrageenan) typically are not added to powder, 2) In addition to the beta carotene, other antioxidants, such as mixed tocopherols and ascorbyl palmitate, can be added to help maintain the oxidative quality of the product during any subsequent spray drying process, and 3) The LCPs are added after mixing the slurries, rather than to the oil slurry.

A protein in water slurry is prepared as was described above for liquid product manufacture.

The carbohydrate/mineral slurry, protein in water slurry and oil slurry are blended together in a similar manner as described for liquid product manufacture. After pH adjustment of the completed blend, LCPs are then added to the blended slurry with agitation. Desirably, the LCPs are slowly metered into the product as the blend passes through a conduit at a constant rate just prior to homogenization (in-line blending).

After deaeration, ultra-high temperature heat treatment, emulsification and homogenization, the processed blend may be evaporated to increase the solids level of the blend to facilitate more efficient spray drying. The blend then passes through a preheater and a high pressure pump and is spray dried using conventional spray drying technology. The spray dried powder may be agglomerated, and then is packaged into metal or plastic cans or foil/laminate pouches under vacuum, nitrogen, or other inert environment.

Variations on any of these manufacturing processes are known to or will be readily apparent to those skilled in the art. It is not intended that the invention be limited to any particular process of manufacture. The full text of all US Patents mentioned herein is incorporated by reference.

Gastric and Intestinal Enzymes

The enzymes used for the in vitro digestion described herein were produced in accordance with United States Pharmacopeia standards. The activity of the enzymes is therefore consistent from lot to lot. The United States Pharmacopeia (USP) is a non-government organization that promotes the public health by establishing state-of-the-art standards to ensure the quality of medicines and other health care technologies. These standards are developed by a process of public involvement and are accepted worldwide. The standards developed by USP are published in the *United States Pharmacopeia* and the *National Formulary* (*USP-NF*), which are recognized in the Federal Food, Drug, and Cosmetic Act (21 U.S.C. § 321 et seq.).

Enzymes suitable for use in the method described herein include, but are not limited to, pepsin, peptidases, pancreatin proteinase, papain, trypsin and chymotrypsin.

In Vitro Protein Digestion

The in vivo digestive process is difficult to reproduce exactly. However, several conditions that exist in vivo can be reproduced in vitro. In vitro digestibility assays should be conducted under conditions that are as close as possible to in vivo conditions. For example, the pH and enzymes of the digestive system should be incorporated into the in vitro digestion process. Similarly, the in vitro digestion should be of a duration corresponding to the time proteins reside in the digestive tract. The in vitro digestion process described below mimics the pH and make up of gastric and intestinal enzymes of young infants. The time of in vitro digestion also mimics the time required for food to pass through the digestive tract of young infants. Protein digestions of nutritional products were prepared by the following procedure:

Prepare 80 mL of a sample of nutritional product by obtaining a volume of ready to feed nutritional product, reconstitution of powder or dilution of liquid concentrate.

Quantitatively transfer the suspension into a 100 mL volumetric flask and dilute to 100 mL with water. (The suspension should be prepared so that the 100 mL volumetric flask contains approximately 1.625 grams of protein, and so that the aliquot pipetted into the 20-mL screw cap vial contains approximately 0.1625 grams of protein. The quality of the assay results depend, to some extent, upon the use of a constant ratio of enzyme to sample protein.)

Pipette 10 mL of the diluted sample into a 20 mL screw-cap vial.

Adjust the pH of the 10 mL aliquot to 4.5 with 1 M hydrochloric acid.

Add 32 mg of USP Pepsin (U.S. Pharmacopeia, 12601 Twinbrook Parkway, Rockville, Md. 20852) and stir to thoroughly suspend the pepsin.

Incubate in vial at 37° C. for thirty minutes.

Raise the pH to 7.0 with 0.5 M $NaHCO_3$.

Add 3.0 mL of freshly prepared suspension of USP Pancreatic Protease Amylase (U.S. Pharmacopeia, 12601 Twinbrook Parkway, Rockville, Md. 20852) at 25 mg/mL in 0.1 M $NaHCO_3$. Stir to thoroughly suspend the enzyme.

Incubate the vial at 37° C. for sixty minutes.

Immerse the vial in a boiling water bath for 4 minutes. Cool to room temperature.

Quantitatively transfer the resulting digest into a tared 25 mL volumetric flask using water to assist the transfer. Dilute the digest in the flask with water and record the weight.

Reagent blanks are digested alongside the nutritional samples for use in calculating the resulting total and soluble portions of the amino acids in the digested samples.

Separate aliquots of the digestion were taken to determine amino acid profile and trytophan concentrations. However, if amino acid profile and tryptophan concentrations are to be determined from the same digestion aliquot, no separation steps are required.

Amino Acid Profile

Prior to testing for total amino acid profile, 100 μL of the digest was transferred by pipette into a tared 2 mL ampule, and the weight recorded. 2.0 mL of 6 M HCl were added and the ampule was placed under nitrogen blanket, sealed and heated at 110° C. for 22 hours. The digest was then evaporated to dryness then resuspended in 2 mL of Na—S buffer. The resuspension was filtered through a Gelman Acrodisc (0.45 um, Gelman P/N 4497).

Prior to testing for soluble amino acid profile, 10 mL of the digest was transferred by pipette into a tared 50 mL centrifuge tube. 10 mL of 24% trichloroacetic acid were added, the tube capped and mixed well. The weight of the tube contents was recorded. The tube and contents were centrifuged at 3000 times gravity for thirty minutes, the liquid was then filtered through Whatman No. 41 paper. 200 μL of the filtrate was transferred by pipette into a tared 2 mL ampule, and the weight of the sample was recorded. As with the testing of total amino acid, 2.0 mL of 6 M HCl were added and the ampule was placed under nitrogen blanket, sealed and heated at 110° C. for 22 hours. The digest was then evaporated to dryness, then resuspended in 2 mL of Na—S buffer. The resuspension was filtered through a Gelman Acrodisc (0.45 um, Gelman P/N 4497).

If soluble and total amino acid profiles are to be determined from the same digestion aliquot, a separation step (such a centrifugation) is not required.

Proteins are hydrolyzed to their constituent amino acids by acid hydrolysis, and the acid hydrolyzate is tested by an automated amino acid analyzer (Model 6300 Amino Acid Analyzer, Beckman Instruments, Inc., Palo Alto, Calif.). The analyzer uses ion exchange chromatography to separate the individual amino acids, and post-column derivatization with ninhydrin to generate amino acid derivatives which are then detected and quantified by a colorimeter.

Tryptophan Determination

Tryptophan determinations were made by the method described by S. E. Garcia and J. H. Baxter in *Determination of Tryptophan Content in Infant Formulas and Medical Nutritionals*, J AOAC Int 1992 November-December; 75(6):1112-9, incorporated herein by reference.

For tryptophan determination of total protein, 3.0 mL of digest was transferred to a 50-mL volumetric flask. 1.0 mL of pronase solution (1.7 mg/mL in 0.05 M TRIS, pH 7.5) was added and the volume diluted to 50 mL with pH 7.5 buffer. The 50 mL solution was then incubated at 50° C. for six hours. Tryptophan was then determined by HPLC procedure.

For tryptophan determination of soluble protein, 6.0 mL of the filtrate as prepared for soluble amino acid determination was transferred by pipette to a 50 mL beaker. 30 mL of 0.05 M TRIS, pH to 7.5, were added. The pH was adjusted to 7.5 using 45% potassium hydroxide solution. As with the testing of tryptophan for total protein, 1.0 mL of pronase solution (1.7 mg/mL in 0.05 M TRIS, pH 7.5) was added and the volume diluted to 50 mL with pH 7.5 buffer. The 50 mL solution was then incubated at 50° C. for six hours. Tryptophan was then determined by HPLC procedure.

HPLC System for Tryptophan Determination

Column: YMC ODS-AQ, 4.6×250 mm, 120A, 5 um, Waters #AQ12S052546WT.

Mobile Phase A: 900 mL 0.02 M $KH_2PO_4$, 100 mL acetonitrile; pH 3.1 with $H_3PO_4$.

Mobile Phase B: 200 mL laboratory water, 800 mL acetonitrile.

Flowrate: 0.5 mL/minute.

Temperature: 20° C.

Detection: UV at 280 nm, 214 nm.

Injection: 10 µL

Run time: 50 minutes

Elution Program: 0% B from 0-5 minutes, 0-25% B from 5-34 minutes, 25-100% B from 34-35 minutes, 100% B from 35-37 minutes, 100-0% B from 37-38 minutes.

Standard solutions: Abbott Laboratories PPD L-Tryptophan at about 28 mg/L (High Standard), about 14 mg/L (Middle Standard), and about 7 mg/L (Low Standard) in laboratory water.

Calculation of Protein Digestibility

Add the amino acid profile concentrations and tryptophan concentration for the Reagent Blank Total Protein. Designate this values as "RT".

Add the amino acid profile concentrations and tryptophan concentration for the Reagent Blank Soluble Protein. Designate this value as "RS".

Add the amino acid profile concentrations and tryptophan concentration obtained for the Sample Digestion Total Protein. Designate this value as "IT".

Add the amino acid profile concentrations and tryptophan concentration obtained for the Sample Digestion Soluble Protein. Designate this value as "IS".

Calculate Protein Digestibility as follows:

$$\text{Protein Digestibility} = \frac{IS - RS}{IT - RT} \times 100$$

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While some potential advantages and objects have been expressly identified herein, it should be understood that some embodiments of the invention may not provide all, or any, of the expressly identified advantages and objects.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

The following examples further illustrate the invention but, of course, should not be construed as in any way limiting its scope.

Example 1

Three powdered Arla whey protein hydrolyzates (WPH), Aria WPH Alternates 1, 2 and 3, were obtained from Arla Foods Ingredients amba Nr.Vium DK-6920 Videbaek Denmark. 80 mL of reconstituted powdered WPHs, containing about 1.625 grams of protein and 80 mL of reconstituted Nestle GOOD START™, also containing about 1.625 grams of protein, were digested in vitro alongside a reagent blank according to the process described herein. Amino acid profile and tryptophan concentrations were determined for the total digestion and the soluble portion of the digestion as described herein. The amino acid profiles are shown in Table 1. A comparison of protein digestibility is shown in Table 2.

TABLE 1

Amino Acid Profile of Example 1 Digested Samples. Concentration is in grams of amino acid per 100 grams of total protein.

| Amino Acid | Arla 1 | Arla 2 | Arla 3 | Nestle GOOD START ™ |
|---|---|---|---|---|
| ASX | 9.70 | 11.7 | 10.1 | 10.3 |
| THR | 6.57 | 7.73 | 6.87 | 7.11 |
| SER | 4.46 | 5.21 | 4.64 | 4.69 |
| GLX | 16.2 | 19.6 | 17.0 | 16.7 |
| PRO | 5.73 | 6.88 | 5.97 | 5.83 |
| GLY | 1.34 | 1.64 | 1.33 | 1.32 |
| ALA | 4.46 | 5.22 | 4.69 | 4.74 |
| CYS | 1.66 | 2.03 | 1.81 | 0.99 |
| VAL | 4.97 | 5.90 | 5.54 | 5.34 |
| MET | 1.64 | 1.87 | 1.66 | 1.69 |
| ILE | 5.38 | 6.45 | 6.11 | 6.26 |
| LEU | 8.84 | 10.2 | 9.88 | 9.40 |
| TYR | 2.40 | 2.59 | 2.63 | 2.31 |
| PHE | 2.64 | 2.91 | 3.02 | 2.76 |
| HIS | 1.70 | 1.94 | 1.82 | 1.76 |
| LYS | 8.78 | 10.3 | 9.06 | 8.69 |
| ARG | 2.07 | 2.44 | 2.26 | 2.06 |
| TRP | 1.36 | 1.27 | 1.50 | 1.22 |
| TOTAL | 89.9 | 105.9 | 95.9 | 93.2 |

Note:
TRP was determined by HPLC. These values are based on total protein concentrations of 77.0%, 78.0%, 78.5%, and 12.3% for Arla 1, Arla 2, Arla 3 and GOOD START ™ Powder, respectively.

TABLE 2

Comparison of Protein Digestibility.

| Whey Protein Product | Soluble Protein After Digestion (as grams amino acid per 100 grams of protein*) |
|---|---|
| Nestle GOOD START ™ | 93.2 |
| Aria WPH Alternate 1 | 89.9 |
| Aria WPH Alternate 2 | 105.9 |
| Aria WPH Alternate 3 | 95.9 |

*i.e., as grams of total amino acids in soluble protein per 100 grams of total sample protein.

Because WPH digestibility may be lowered by the infant formula manufacturing process, definitive conclusions regarding the digestibility of this nutritional product are better drawn from comparisons of infant formulas.

Example 2

Three samples of SIMILAC™ with low iron and three samples of Nestle GOOD START™ powders were each reconstituted with water and 80 mL of each reconstitution contained about 1.625 grams of protein. The formula samples were digested in vitro alongside a reagent blank according to the process described herein. The in vitro digestion process described earlier, mimics the digestive system of young infants in the parameters of pH, enzymes present, and time of digestion. Amino acid profile and tryptophan concentrations were determined for the total digestion and the soluble portion of the digestion as described herein. An example of an amino acid profile is shown in Table 3. Calculations of protein digestibility as described herein were conducted. A comparison of protein digestibility is shown in Table 4.

TABLE 4

Amino Acid Profile of Example 2 Digested Samples. Concentrations are as mg/L of Sample Suspension.

| Amino Acid | Reagent Blank | | Infant Formula | |
|---|---|---|---|---|
| | Total Protein | Soluble Protein | Total Protein | Soluble Protein |
| ASX | 430 | 375 | 1914 | 1703 |
| THR | 161 | 134 | 1065 | 939 |
| SER | 204 | 173 | 1082 | 981 |
| GLX | 434 | 391 | 3693 | 3428 |
| PRO | 152 | 130 | 1562 | 1232 |
| GLY | 242 | 209 | 558 | 462 |
| ALA | 167 | 141 | 825 | 739 |
| CYS | 45 | 29 | 181 | 136 |
| VAL | 170 | 137 | 1218 | 1003 |
| MET | 34 | 27 | 407 | 372 |
| ILE | 142 | 113 | 1107 | 954 |
| LEU | 182 | 143 | 1861 | 1580 |
| TYR | 150 | 127 | 850 | 757 |
| PHE | 112 | 90 | 825 | 650 |
| HIS | 88 | 75 | 496 | 420 |
| LYS | 237 | 218 | 1613 | 1533 |
| ARG | 224 | 205 | 733 | 676 |
| TRP | 85 | 69 | 306 | 244 |
| Total | 3259 | 2786 | 20,296 | 17,809 |

$$\text{Protein Digestibility} = \frac{17,809 - 2,786}{20,296 - 3,259} \times 100 = 88.2\%$$

TABLE 4

Comparison of Protein Digestibilities of SIMILAC ™ and Nestle GOOD START ™ Powders.

| Infant Formula | In Vitro Protein Digestibility |
|---|---|
| Nestle GOOD START ™ Powder #107EWGS0159S | 89.0% +/− 1.2% (n = 3) |
| SIMILAC ™ with Low Iron Powder #61927RE | 87.8% +/− 0.6% (n = 3) |

What is claimed is:

1. A method for determining the digestibility of proteins in a nutritional product comprising the steps of:
    a) providing a sample of a nutritional product that contains protein and a reagent blank;
    b) separately digesting the sample of a nutritional product and the reagent blank with at least one protein-degrading enzyme;
    c) terminating each said digestion process to obtain a digested sample and a digested reagent blank;
    d) removing a first portion from each of said digested sample and said digested reagent blank in step c);
    e) determining the concentrations of at least 18 different amino acids, including tryptophan, for each of said first portions obtained from said digested sample and said digested blank in step d);
    f) removing a second portion from each of said digested sample and said digested reagent blank in step c);
    g) separating each of said second portions from step f) into a liquid phase and a solid phase;
    h) determining the concentrations of said at least 18 different amino acids, including tryptophan, soluble in the liquid phases obtained from said second portions of said digested sample and said digested reagent blank in step g);

i) calculating the percent digestibility of the protein in the nutritional sample by:
   1) adding the concentrations of said at least 18 different amino acids, for each of said first portions obtained from said digested sample and said digested reagent blank in step e) to provide a sum that is the total amino acid concentration in each of said digested sample and said digested blank;
   2) determining the difference between the total amino acid concentrations of the first portions of each of digested sample and the digested reagent blank in step 1;
   3) adding the concentrations of said at least 18 different amino acids soluble in each of the liquid phases obtained from said second portions of said digested sample and said digested reagent blank in step h); to provide a sum that is the soluble amino acid concentration in each of said second portions of said digested sample and said digested blank;
   4) determining the difference between the soluble amino acid concentrations of the said second portions from said digested sample and the digested reagent blank;
   5) dividing the difference between the soluble amino acid concentrations of step 4) by the difference between the total amino acid concentrations of step 2) to obtain a quotient;
   6) multiplying the quotient by 100, thereby determining the protein digestibility of a nutritional sample.

2. The method of claim 1, wherein the method of separating in step g) is selected from the group consisting of acidification, precipitation, centrifugation, filtration, and a combination of centrifugation and filtration.

3. The method of claim 1, wherein the nutritional product is infant formula.

4. The method of claim 1, wherein the digesting step uses one or more enzymes to mimic the environment of a human gastrointestinal tract.

5. The method of claim 4 wherein the at least one protein-degrading enzyme is selected from the group consisting of pepsin, peptidases, pancreatin proteinase, pancreatic protease amylase, papain, trypsin and chymotrypsin.

6. The method of claim 1 wherein the step of digesting the sample and the reagent blank in step b) further comprises:
   placing each of said sample and said reagent blank in an aqueous solution to obtain a sample mixture and a reagent blank mixture;
   adjusting the pH of each said mixture to about 4.5;
   adding pepsin to each said mixture;
   incubating the mixtures;
   increasing the pH of each said mixture to about 7.0;
   adding pancreatin proteinase to each said mixture; and
   incubating said mixtures.

7. The method of claim 6, wherein the pepsin has been prepared by established standards, designed to ensure lot-to-lot consistency in enzyme activity.

8. The method of claim 6, wherein the pancreatin proteinase has been prepared by established standards, designed to ensure lot-to-lot consistency in enzyme activity.

9. The method of claim 1 wherein the step c) of terminating the digestion comprises immersing the sample in a boiling water bath.

10. The method of claim 1, wherein said protein-degrading enzyme has been prepared by established standards, designed to ensure lot-to-lot consistency in enzyme activity.

11. The method of claim 1, wherein said at least 18 different amino acids are the individual building blocks of proteins.

* * * * *